(12) United States Patent
Gribble et al.

(10) Patent No.: US 8,518,965 B2
(45) Date of Patent: Aug. 27, 2013

(54) COMPOSITIONS AND METHODS FOR TREATING CANCER

(75) Inventors: Gordon W. Gribble, Lebanon, NH (US); Dmitry A. Androsov, Kolpino (RU)

(73) Assignee: Trustees of Dartmouth College, Hanover, NH (US)

( * ) Notice: Subject to any disclaimer, the term of this patent is extended or adjusted under 35 U.S.C. 154(b) by 9 days.

(21) Appl. No.: 13/388,485

(22) PCT Filed: Jul. 13, 2010

(86) PCT No.: PCT/US2010/041784
§ 371 (c)(1),
(2), (4) Date: Mar. 8, 2012

(87) PCT Pub. No.: WO2011/016952
PCT Pub. Date: Feb. 10, 2011

(65) Prior Publication Data
US 2012/0165365 A1    Jun. 28, 2012

Related U.S. Application Data

(60) Provisional application No. 61/231,102, filed on Aug. 4, 2009.

(51) Int. Cl.
*A61K 31/473* (2006.01)
*A61K 31/4709* (2006.01)
*A61P 35/00* (2006.01)
*C07D 401/12* (2006.01)
*C12N 5/09* (2010.01)

(52) U.S. Cl.
USPC ........... 514/297; 514/313; 435/375; 546/106; 546/160

(58) Field of Classification Search
USPC ................ 514/297, 313; 435/375; 546/106, 546/160
See application file for complete search history.

(56) References Cited

U.S. PATENT DOCUMENTS

| | | | |
|---|---|---|---|
| 5,886,185 A | 3/1999 | Chou et al. | 546/106 |
| 6,187,787 B1 | 2/2001 | Gribble et al. | 514/297 |
| 2006/0088934 A1 | 4/2006 | Greene et al. | 435/368 |
| 2009/0176745 A1 | 7/2009 | Arbiser | 514/114 |

OTHER PUBLICATIONS

Jaycox et al. "Potential DNA bis-Intercalating Agents: Synthesis and Antitumor Activity of Novel, Conformationally Restricted bis(9-Aminoacridines)" Journal of Heterocyclic Chemistry 1987 vol. 24:1405-1408.

*Primary Examiner* — Raymond Henley, III
(74) *Attorney, Agent, or Firm* — Licata & Tyrrell P.C.

(57) ABSTRACT

The present invention embraces bis-acridine and bis-quinoline intercalators having a bis(4-aminophenyl)ether tether, and diglycolate salts thereof, for selectively decreasing colon cancer and glial cell proliferation and preventing or treating colon cancers and gliomas.

22 Claims, 2 Drawing Sheets

COMPOSITIONS AND METHODS FOR TREATING CANCER

This application is a U.S. National Stage Application of PCT/US2010/041784 filed Jul. 13, 2010 and claims the benefit of priority of U.S. Provisional Application No. 61/231,102, filed Aug. 4, 2009, the contents of each of which are incorporated herein by reference in their entirety.

BACKGROUND OF THE INVENTION

Glial tumors, the most prevalent and morbid of which is astrocytoma and its aggressive derivative glioblastoma multiforme, are the most common cancers of the adult central nervous system. They are also among the least treatable cancers, with a 5 year survival after initial diagnosis of <10% for tumors initially diagnosed at the grade 3 (anaplastic astrocytoma) or 4 (glioblastoma) stages. The currents treatment of glioma and glioblastoma are lacking, and achieve only palliation and short-term increments in survival. They include surgical resection, wherein ultimate recurrence rates are over 90%, as well as radiation therapy and chemotherapies that include cisplatin, BCNU and other mitotic inhibitors. The benefits of these current therapies are brief and temporary, and none are curative (e.g., Schiffer (1997) *Brain Tumors. Biology, Pathology, and Clinical References*, Springer-Verlag, New York, Berlin, Heidelberg). Accordingly, there is a need in the art for more effective treatments of glial tumors.

SUMMARY OF THE INVENTION

The present invention features a method for selectively decreasing colon or glial tumor cell proliferation by contacting a colon or glial tumor cell with an effective amount of a compound of Formula I:

wherein dashed lines represent bonds that are independently present or absent. According to one embodiment, the compound of Formula I is a diglycolate salt. In another embodiment, the glial tumor cell is an astrocytoma tumor cell, ependymal tumor cell, glioblastoma multiforme tumor cell, or primitive neuroectodermal tumor cell.

The present invention also features a method for increasing survival time of a subject with cancer by administering to a subject with colon cancer or glioma an effective amount of a compound of Formula I, thereby increasing the survival time of the subject as compared to a subject not receiving said treatment. In one embodiment, the compound of Formula I is a diglycolate salt. In other embodiments, the glioma is an astrocytoma, ependymal tumor, primitive neuroectodermal tumor, or glioblastoma multiforme (e.g., in the brain or spinal cord). In further embodiments, the subject being treated is a mammal such as a human, wherein said administering is carried out orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes.

The present invention also embraces a method for treating colon cancer or glioma by administering to a subject in need thereof an effective amount of a compound of Formula I, thereby treating the subject's colon cancer or glioma. In one embodiment, the compound of Formula I is a diglycolate salt. In other embodiments, the glioma is an astrocytoma, ependymal tumor, primitive neuroectodermal tumor, or glioblastoma multiforme (e.g., in the brain or spinal cord). In further embodiments, the subject being treated is a mammal such as a human, wherein said administering is carried out orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes.

The present invention also features a composition including:

wherein dashed lines represent bonds that are independently present or absent, and wherein, according to some embodiments, said composition can further include a pharmaceutically acceptable carrier. When used therapeutically, it is desirable that said composition be formulated for administration orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes.

DETAILED DESCRIPTION OF THE INVENTION

The present invention features anti-cancer compounds, pharmaceutical compositions and methods for decreasing colon or glial tumor cell proliferation, increasing survival, and treating colon cancer or glioma. Specifically, bis-acridine or bis-quinoline intercalators having a bis(4-aminophenyl) ether tether have now been shown to have a unique structure that imparts anti-cancer activity, which is not achieved by derivatives of the same. Moreover, compounds of the invention have been shown to exhibit low toxicity and particular selectivity for decreasing colon cancer and glial cell proliferation thereby making them useful in the treatment of colon cancers and gliomas.

Compounds embraced by the present invention are represented by Formula I:

Formula I wherein dashed lines represent bonds (A-E) that are independently present or absent. When dashed lines are present, a compound of Formula I can include one or more of bonds A-E, and hence one to four additional carbons, with the appropriate valencies. As will be appreciated by one skilled in the art, bonds B, C, and/or D are only present when one or both of bonds A or E are present. For example, compounds of the invention can include, bond A, bonds A-B, bonds A-C, bonds A-D, bonds A-E, bonds B-E, bonds C-E, bonds D-E, bond D, or bonds A-B and D-E. In one embodiment, a compound of the invention includes bond E. In another embodiment, a compound of the invention includes bonds A-E. Compounds of Formula I can be prepared and purified as described herein or using any other suitable methodology routinely practiced in the art.

In one embodiment, the compound of the invention has the structure:

(D11B)

In another embodiment, the compound of the invention has the structure:

(D245B)

In a further embodiment, the compound of the invention has the structure:

(D288)

While compounds of Formula I are soluble in water+TWEEN 80, according to particular embodiments, a compound of Formula I is prepared in the form of a diglycolate salt. A diglycolate salt of a compound of Formula I refers to:

wherein dashed lines represent bonds that are independently present or absent. As compared to other salt forms, a diglycolate salt of D11B has been found to exhibit excellent solubility and stability in water+CREMOPHOR EL; water+TWEEN 80; or water+DMSO solutions, with concentrations of 10 to 45 mg/ml achievable.

As demonstrated herein, D245B and D288 have $IC_{50}$ values (i.e., the concentration of an inhibitor that is required for 50% inhibition of cell growth) at least 7-fold lower than the $IC_{50}$ values of structural derivatives (see Table 21). Likewise, D11B significantly exceeds the $IC_{50}$ values of structural derivatives (see Table 18) and exhibits $IC_{50}$ values approximately 10-fold lower for colon and glioblastoma cells as compared to breast cancer cells. In so far as tumor cell inhibition was selective for colon and glioma tumor cells, the present invention features a method for selectively decreasing colon or glial tumor cell proliferation using a compound of the invention. According to this method, a colon or glial tumor cell is contacted with a compound of Formula I, or a diglycolate salt thereof, thereby decreasing or inhibiting tumor cell growth as compared to a control, e.g., a tumor cell not contacted with the said compound. A glial tumor cell is intended to mean a tumor cell of the central nervous system, including astrocytomas, ependymal tumors, glioblastoma multiforme, and primitive neuroectodermal tumors. A colon tumor cell is intended to mean a tumor cell of the colon, rectum or appendix. In some embodiments, the tumor cell is contacted in vitro. In other embodiments, the tumor cell is contacted in vivo.

Inhibition of colon or glial tumor cell proliferation finds application in the treatment of colon cancer or glioma. In this respect, the present invention also embraces methods of treating colon cancer or glioma in a subject and increasing survival time. The methods involve administering an effective amount of a compound of Formula I, or a diglycolate salt thereof, to a subject in need thereof to treat the colon cancer or glioma or increase survival time.

As used herein, colon cancer, also called colorectal cancer or large bowel cancer, includes cancerous growths in the colon, rectum and appendix. Subjects benefiting from treatment include those with colon cancer (e.g., those diagnosed through colonoscopy), as well as subjects exhibiting clinical signs or symptoms of colon cancer (e.g., a change in bowel habit, lower gastrointestinal bleeding, increased presence of mucus, and/or bowel obstruction).

Glioma refers to a cancer of the brain that begins in glial cells (i.e., cells that surround and support nerve cells and includes oligodendrocytes, astrocytes, microglia, and ependymal cells). In this respect, gliomas embraced by the present invention include astrocytomas, ependymal tumors, glioblastoma multiforme, and primitive neuroectodermal tumors. Subjects benefiting from treatment according to the invention include subjects with a glioma, or subjects suspected of having a glioma, as evidenced by the presence of headaches, nausea and vomiting, seizures, loss of vision, pain, weakness, numbness in the extremities, and/or cranial nerve disorders as a result of increased intracranial pressure. In particular embodiments, the glioma being treated is glioblastoma multiforme. In accordance with this embodiment, the glioblastoma multiforme can be in the brain or spinal cord.

As used herein, treatment of cancer encompasses either reducing the growth of a tumor in the subject, reducing the clinical symptoms associated with tumor growth in the subject, and/or increasing survival time as compared to a subject not receiving treatment. For the purposes of the present invention, "treatment" refers to both therapeutic treatment and prophylactic or preventative measures. As such, those in need of treatment include those already with the disorder as well as those prone to have the disorder (e.g., by genetic predisposition or exposure to carcinogenic agents). Subjects who can be treated in accordance with the present invention include mammals, such as humans, domestic and farm animals, and zoo, sports, or pet animals, e.g., dogs, horses, cats, cows, etc. Preferably, the mammal herein is human.

Effective amounts of a compound of Formula I, or a diglycolate salt thereof, will depend upon the mode of administration, frequency of administration, nature of the treatment, age and condition of the individual to be treated, and the type of pharmaceutical composition used to deliver the compound into a living system. In this respect. effective intracerebral levels of a compound of Formula I, or a diglycolate salt thereof, may range from 50 nM to 5 µM, depending upon the compound, system, and experimental and clinical endpoints. While individual doses vary, optimal ranges of effective amounts can be determined by one of ordinary skill in the art. For example, the safe and effective dosages identified in clinical trials can be considered when selecting dosages for treatments according to the present invention.

Compounds of Formula I, or diglycolate salts thereof, for use according to the methods of the present invention can be administered alone or as a pharmaceutical composition, which includes the compound(s) and a pharmaceutically-acceptable carrier. A pharmaceutical composition can include suitable excipients, or stabilizers, and can be in solid or liquid form such as, tablets, capsules, powders, solutions, suspensions, or emulsions. Typically, the composition will contain from about 0.01 to 99 percent, preferably from about 5 to 95 percent of active compound(s), together with the carrier.

A compound of Formula I, or a diglycolate salt thereof, when combined with pharmaceutically or physiologically acceptable carriers, excipients, or stabilizers, whether in solid or liquid form such as, tablets, capsules, powders, solutions, suspensions, or emulsions, can be administered orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes, such as, that of the nose, throat, and/or bronchial tubes (i.e., inhalation).

For most therapeutic purposes, a compound of Formula I, or a diglycolate salt thereof, can be administered orally as a solid or as a solution or suspension in liquid form, via injection as a solution or suspension in liquid form, or via inhalation of a nebulized solution or suspension. The solid unit dosage forms can be of the conventional type. The solid form can be a capsule, such as an ordinary gelatin type containing the compound(s) of the present invention and a carrier, for example, lubricants and inert fillers such as, lactose, sucrose, or cornstarch. In another embodiment, compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

For injectable dosages, solutions or suspensions of a compound of the invention, or a diglycolate salt thereof, can be prepared in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose, and related sugar solution, and glycols, such as propylene glycol or polyethylene glycol, are preferred liquid carriers, particularly for injectable solutions.

For use as aerosols, a compound of the invention, or a diglycolate salt thereof, in solution or suspension may be packaged in a pressurized aerosol container together with suitable propellants, for example, hydrocarbon propellants like propane, butane, or isobutane with conventional adjuvants. The compounds of the present invention also can be administered in a non-pressurized form such as in a nebulizer or atomizer.

For transdermal routes, a compound of the invention, or a diglycolate salt thereof, is present in a carrier which forms a composition in the form of a cream, lotion, solution, and/or emulsion. The composition can be included in a transdermal patch of the matrix or reservoir type as are conventional in the art for this purpose.

It is also contemplated that administration of a compound of the invention, or a diglycolate salt thereof, can be carried out in combination with other suitable therapeutic treatments which are useful for treating colon cancer or glial tumors. For example, a composition of the invention can be combined with surgery, radiotherapy, and/or chemotherapy (e.g., 5-fluorouracil, leucovorin, and oxaliplatin) in the treatment of colon cancer. Similarly, a composition of the invention can be combined with surgery, radiation therapy, and/or chemotherapy (e.g., Temozolomide) in the treatment of a glioma.

The invention is described in greater detail by the following non-limiting examples.

EXAMPLE 1

Synthesis and Characterization of D11B

Preparation of D11B (Scheme 1).

A mixture of 9-chloroacridine 3 gr. (2.1 equiv.; 14.09 mmol) and bis(4-aminophenyl)ether 1.34 gr. (1 equiv.; 6.7 mmol) in 150 ml of iso-propanol was stirred and refluxed for 12 hours. The resulting suspension was cooled to room temperature, filtered, and washed with iso-propanol (3×50 ml). Drying at room temperature afforded D11B×2HCl. Dihydrochloride was suspended in 50 ml of MeOH and a solution of $Na_2CO_3$ 2.84 gr. (4 equiv.; 26.8 mmol) in 50 ml of water was added. The mixture was refluxed for 1 hour, and methanol was evaporated. Product was filtered and washed with water (3×50 ml). Drying at room temperature gave 94% of D11B as an orange powder, m.p.=248-250° C.

Preparation of D11B.

D11B 5.54 gr. (1 equiv.; mw=554.66 gr/mol; v=10 mmol) was suspended in iso-propanol (V=400 ml) and concentrated HCl (V=3.3 ml; 4 equiv.; d=1.19 gr/ml; N=12.1 mol/l) was added to the suspension. The resulting slurry was heated to reflux, stirred for 10 min and filtered hot. Yellow D11B dihydrochloride was suspended in 200 ml of MeOH and a solution of $Na_2CO_3$ 4.24 gr. (4 equiv.; mw=106 gr/mol, v=40 mmol) in water (200 ml) was slowly added to the suspension. The resulting slurry was heated to reflux, stirred for 10 min and filtered hot to afford D11B. The procedure was repeated twice. Drying at room temperature gave pure D11B. Yield 86.6%, orange solid, m.p.=266-267° C.

SCHEME 1

Characterization of D11B. The solubility of D11B in different solvents was analyzed (Table 1).

TABLE 1

| Solvent | Solubility (mg/ml), 25° C. |
| --- | --- |
| DMSO | ~100 |
| DMF | ~20 |
| PEG-400 | ~12[a] |
| MeOH | ~1 |
| AcOH | ~0.01 |
| AcOH—$H_2O$ (1-1) | >1.1 |
| AcOH—$H_2O$ (9-1) | >13 |
| $CHCl_3$ | 0.12 |
| $H_2O$ | negligible |
| $Na_2HPO_4$-citric acid buffer (pH = 4) | negligible (<0.1 mg/ml) |
| $Na_2HPO_4$-citric acid buffer (pH = 4) | negligible (<0.1 mg/ml) |

[a] Heating to 100° C. was required.

The solubility of D11B in various combinations of solvents was also analyzed. For example, the solubility of D11B in 5% dextrose in water was negligible as was the solubility in saline (0.9% NaCl in water). For the analysis of co-solvents, stock solutions were prepared by dissolving D11B in a corresponding solvent. Stock solutions of D11B in dimethylsulfoxide (DMSO) were prepared at 25° C., and stock solutions of D11B in PEG-400, CREMOPHOR® EL and Polysorbate 80 were prepared at 100° C. Injection solutions, in water (0.3 mg/ml), were prepared by dropwise addition of the stock solution to a required volume of vigorously stirred hot water (80° C.). It was important to follow this order, as precipitation of D11B occurs. Thus, fast addition of the stock solution to water could cause precipitation, as could the addition of water to the stock solution. The characteristics of the D11B in water+polysorbate 80 (d=1.06-1.09) as a co-solvent; water+ CREMOPHOR® EL (d=1.05) as a co-solvent; water+DMSO (d=1.1) as a co-solvent; and water+PEG-400 (d=1.128) as a co-solvent are listed in Tables 2-5, respectively.

TABLE 2

| | |
| --- | --- |
| Stock solution of D11B in Polysorbate 80 | 32.25 mg/ml |
| State of the stock solution | clear |
| Injection solution of D11B in $H_2O$-Polysorbate 80 | 0.3 mg/ml |
| State of the injection solution | clear |

TABLE 2-continued

| | |
|---|---|
| Water volume used to prepare injection solution | 65.67 ml |
| Content of Polysorbate 80 in injection solution | 1 wt. % |

TABLE 3

| | |
|---|---|
| Stock solution of D11B in CREMOPHOR ® EL | 31.5 mg/ml |
| State of the stock solution | clear |
| Injection solution of D11B in H$_2$O-CREMOPHOR ® EL | 0.3 mg/ml |
| State of the injection solution | clear |
| Water volume used to prepare injection solution | 65.67 ml |
| Content of CREMOPHOR ® EL in injection solution | 1 wt. % |

TABLE 4

| | 1 | 2 | 3 | 4 | 5 | 6 |
|---|---|---|---|---|---|---|
| Stock solution of D11B in DMSO (mg/ml) | 20 | 30 | 40.5 | 50 | 70 | 100 |
| State of the stock solution | clear | clear | clear | clear | clear | clear |
| Injection solution of D11B in H2O—DMSO (mg/ml) | 0.3 | 0.3 | 0.3 | 0.3 | 0.3 | 0.3 |
| State of the injection solution | clear | clear | clear | clear | clear | clear |
| Water volume used to prepare injection solution (ml) | 65.67 | 99 | 134 | 165.67 | 232.33 | 332.33 |
| Content of DMSO in injection solution (wt. %) | 1.65 | 1.1 | 0.83 | 0.66 | 0.47 | 0.33 |

TABLE 5

| | 1 | 2 | 3 |
|---|---|---|---|
| Stock solution of D11B in PEG-400 (mg/ml) | 40 | 20 | 12 |
| State of the stock solution | gel | gel | clear |
| Injection solution of D11B in H$_2$O-PEG-400 (mg/ml) | 0.3 | 0.3 | 0.3 |
| State of the injection solution | some precipitation | clear[a] | clear[b] |
| Water volume used to prepare injection solution (ml) | 132.33 | 65.66 | 39 |
| Content of PEG-400 in injection solution (wt. %) | 0.85 | 1.7 | 2.82 |

[a]Precipitate formed after 1 hour.
[b]Precipitate formed after 10 hours.

The results of this analysis indicated that the best solubility and stability of D11B in water solution was achieved using Polysorbate 80 (1% wt) (FDA approved); Cremophor® EL (1% wt) (FDA approved); DMSO as a co-solvent (1-3% wt); and solutions of D11B in water containing PEG-400 (<3% wt.). While solutions of D11B in water containing PEG-400 were not suitably stable, solutions of D11B with a higher content of PEG-400 may be more stable.

EXAMPLE 2

Preparation of Salts of D11B

Preparation of D11B×2AH (Scheme 2).
A suspension of D11B 1 gr. (1 equiv.; 1.8 mmol) and corresponding acid AH (2.1 equiv; 3.78 mmol) in 50 ml of methanol was stirred and refluxed for 1 hour. Methanol was removed under reduced pressure and 50 ml of iso-propanol was added to form an orange suspension. The suspension was stirred for 30 minutes at room temperature and filtered. Orange precipitate was washed with iso-propanol (3×50 ml). Drying at room temperature afforded D11B×2AH as orange solid (see Table 6).

SCHEME 2

TABLE 6

| D11Bx2AH | AH | yield, % | m.p., ° C. |
|---|---|---|---|
| 1 | (structure) | 94 | 95-98 |
| 2 | (structure) | 90 | 270 |
| 3 | (structure) | 90 | 188-190 |
| 4 | (structure) | 85 | 178-180 |
| 5 | (structure) | 82 | 223-224 |

TABLE 6-continued

| D11Bx2AH | AH | yield, % | m.p., °C |
|---|---|---|---|
| 6 | HO-, HO-, HO- substituted benzoic acid (3,4,5-trihydroxybenzoic acid / gallic acid) | 87 | 229-230 |
| 7 | HO-, HO- substituted phenylacetic acid (3,4-dihydroxyphenylacetic acid) | 80 | 206-208 |

The solubility of D11B×2AH in DMSO, PEG-400, EtOH, and buffer was determined (Table 7).

TABLE 7

| | Solubility (mg/ml), 25° C. | | | |
|---|---|---|---|---|
| D11Bx2AH | DMSO | PEG-400$^a$ | EtOH | Buffer (pH = 6) | Buffer (pH = 4) |
| 1 | 31 | >10 | >1 | >0.5, even at 100° C. |
| 2 | 13 | — | | |
| 3 | 38 | — | | |
| 4 | 40 | >10 | | |
| 5 | 45 | 10 | | |
| 6 | 325 | 20 | | |
| 7 | 66 | — | | |

$^a$Samples were dissolved at 100° C.

Additional solubility determinations were carried out with D11B×2AH in water+co-solvents. For this analysis, stock solutions were prepared by dissolving D11B×2AH in a corresponding solvent. Stock solutions of D11B×2AH in DMSO were prepared at 25° C. and stock solutions of D11B×2AH in PEG-400 were prepared at 100° C. Stock solutions of D11B× 2AH in CREMOPHOR® EL or Polysorbate 80 could not be prepared, even at 100° C., due to very low solubility. The only salt which had an acceptable solubility in CREMOPHOR® EL (d=1.05) was D11B diglycolate (Table 8).

Injection solutions in water (0.3 mg/ml) were prepared by dropwise addition of each stock solution to a required volume of vigorously stirred water. It was important to follow this order, otherwise precipitation of D11B×2AH occurred. Thus, fast addition of the stock solution to water could cause precipitation, as could the addition of water to the stock solution.

TABLE 8

| D11bx2AH | Stock solution | Injection solution (0.3 mg/ml) | CREMOPHOR ® EL content |
|---|---|---|---|
| diglycolate (5) | 31.5 mg/ml$^a$ | clear | 1 wt. % |

$^a$Heating to 100° C. was required.

The characteristics of the D11B digluconate (1), D11B diacetate (2), D11B bis(diammoniumcitrate) (3), D11B dilactobionate (4), D11B diglycolate (5), D11B digallate (6) and D11B bis(3,4-dihydroxyphenylacetate) (7) in water+ DMSO (d=1.1) as a co-solvent are listed in Tables 9-15, respectively.

TABLE 9

| | 1 | 2 | 3 |
|---|---|---|---|
| Stock solution of D11B digluconate (1) in DMSO | 22 mg/ml | 31 mg/ml | 55 mg/ml |
| State of the stock solution | clear | clear | fine suspension |
| Injection solution of D11B digluconate (1) in H$_2$O—DMSO | 0.3 mg/ml | 0.3 mg/ml | 0.3 mg/ml |
| State of the injection solution | clear | clear | slightly opalescent |
| Water volume used to prepare injection solution | 72.33 ml | 102.33 ml | 182.33 ml |
| Content of DMSO in injection solution | 1.50 wt. % | 1.06 wt. % | 0.6 wt. % |

TABLE 10

| | 1 | 2 |
|---|---|---|
| Stock solution of D11B diacetate (2) in DMSO | 11 mg/ml | 13.5 mg/ml |
| State of the stock solution | clear | clear |
| Injection solution of D11B diacetate (2) in H$_2$O—DMSO | 0.3 mg/ml | 0.3 mg/ml |
| State of the injection solution | slightly opalescent, almost clear | slightly opalescent |
| Water volume used to prepare injection solution | 72.33 ml | 102.33 ml |
| Content of DMSO in injection solution | 3.0 wt. % | 2.36 wt. % |

TABLE 11

| | 1 |
|---|---|
| Stock solution of D11B bis(diammoniumcitrate) (3) in DMSO | 20 mg/ml |
| State of the stock solution | clear |
| Injection solution of D11B bis(diammoniumcitrate) (3) in H$_2$O—DMSO | 0.3 mg/ml |
| State of the injection solution | instant precipitation of orange solid |
| Water volume used to prepare injection solution | 65.67 ml |
| Content of DMSO in injection solution | 1.36 wt. % |

TABLE 12

| | 1 | 2 |
|---|---|---|
| Stock solution of D11B dilactobionate (4) in DMSO | 20 mg/ml | 40 mg/ml |
| State of the stock solution | clear | clear |
| Injection solution of D11B dilactobionate (4) in H$_2$O—DMSO | 0.3 mg/ml | 0.3 mg/ml |
| State of the injection solution | clear | clear |
| Water volume used to prepare injection solution | 65.67 ml | 132.33 ml |
| Content of DMSO in injection solution | 1.36 wt. % | 0.68 wt. % |

TABLE 13

|  | 1 | 2 |
|---|---|---|
| Stock solution of D11B diglycolate (5) in DMSO | 45 mg/ml | 20 mg/ml |
| State of the stock solution | clear | clear |
| Injection solution of D11B diglycolate (5) in H₂O—DMSO | 0.3 mg/ml | 0.3 mg/ml |
| State of the injection solution | clear | clear |
| Water volume used to prepare injection solution | 149.05 ml | 65.67 ml |
| Content of DMSO in injection solution | 0.64 wt. % | 1.36 wt. % |

TABLE 14

|  | 1 | 2 | 3 | 4 | 5 |
|---|---|---|---|---|---|
| Stock solution of D11B digalate (6) in DMSO (mg/ml) | 325 | 158 | 77 | 39.9 | 20 |
| State of the stock solution | clear | clear | clear | clear | clear |
| Injection solution of D11B digalate (6) in H₂O—DMSO (mg/ml) | 0.3 | 0.3 | 0.3 | 0.3 | 0.3 |
| State of the injection solution | prec. | some prec. instantly | some prec. after 12 h | clear | clear |
| Water volume used to prepare injection solution (ml) | 1082.33 | 525.67 | 255.67 | 132 | 65.67 |
| Content of DMSO in injection solution (wt. %) | 0.1 | 0.21 | 0.43 | 0.83 | 1.65 |

TABLE 15

|  | 1 |
|---|---|
| Stock solution of D11B bis(3,4-dihydroxyphenylacetate) (7) in DMSO | 66 mg/ml |
| State of the stock solution | clear |
| Injection solution of D11B bis(3,4-dihydroxyphenylacetate) (7) in H₂O—DMSO | 0.3 mg/ml |
| State of the injection solution | clear |
| Water volume used to prepare injection solution | 219 ml |
| Content of DMSO in injection solution | 0.5 wt. % |

The characteristics of the D11B digluconate (1), D11B dilactabionate (4), D11B diglycolate (5), and D11B digallate (6) in water+PEG-400 (d=1.128) as a co-solvent are listed in Tables 16.

TABLE 16

| D11Bx2AH | Solubility (mg/ml) | Stock solution (mg/ml) | Injection solution 0.3 (mg/ml) | PEG-400 content (wt. %) |
|---|---|---|---|---|
| digluconate (1) | >10 | — | — | — |
| dilactabionate (4) | >10 | — | — | — |
| diglycolate (5) | 10ᵃ | 10 | clear | 3.38 |
| digallate (6) | 20ᵃ | 20 | clear, precipitate forms after 1 hour | — |

ᵃHeating to 100° C. was required.

As with D11B, all D11Bx2AH salts in 5% dextrose in water showed negligible solubility. Similarly, all D11Bx2AH salts in saline (0.9% NaCl in water) were negligibly soluble.

The overall results of these analyses indicated that the best solubility and stability of D11Bx2AH in water solution were achieved using CREMOPHOR® EL (1% wt) (FDA approved) for D11B diglycolate (5) and DMSO (~3% wt) as a co-solvent for all D11Bx2AH salts. In addition, while solutions of D11Bx2AH in water containing PEG-400 (<3% wt.) can be prepared for some salts (e.g., D11B diglycolate), solubility of D11Bx2AH in other solvents analyzed was very low.

EXAMPLE 3

Synthesis of D11B Derivatives with Variable Bis-Amine Tethers A mixture of 9-cloroacridine 3 gr (2.1 equiv.; 14.09 mmol) and bis-amine (1 equiv.; 6.7 mmol) in 150 ml of iso-propanol was stirred and refluxed for 12 hours (Scheme 3). The resulting suspension was cooled to room temperature, filtered, and washed with iso-propanol (3×50 ml). Drying at room temperature afforded bis-acridinex2HCl. The dihydrochloride was suspended in 50 ml of MeOH and a solution of Na₂CO₃ 2.84 gr (4 equiv.; 26.8 mmol) in 50 ml of water was added. The mixture was refluxed for 1 hour, and methanol was evaporated. Product was filtered and washed with water (3×50 ml). Drying at room temperature gave the corresponding bis-acridines in Table 17.

SCHEME 3

TABLE 17

| Compound H$_2$N—R—NH$_2$ | | Yield (%) |
|---|---|---|
| D15 |  | 82% dark red solid |
| D16 |  | 62% yellow solid |
| D17 |  | 71% yellow solid |
| D18 |  | 91% dark yellow solid |
| D19 |  | 85% yellow solid |
| D20 |  | 91% yellow solid |
| D21 |  | 78% brown solid |
| D23 |  | 85% yellow solid |
| D24 |  | 77% orange solid |
| D25 |  | 94% dark red solid |
| D35 |  | 91% orange solid |

EXAMPLE 4

In Vitro Anticancer Activity of D11B and D11B Derivatives

The objective of this analysis was to compare the anticancer activity of D11B to the anticancer activity of D11B derivatives on three human cancer cell lines (ADR-RES human breast cancer cells, HCT116 human colon cancer cells and SF 295 human glioblastoma cells).

Methods.

NCI/ADR-RES human breast cancer cells (500 cells), HCT116 human colon cancer cells (400 cells) or SF 295 human glioblastoma cells (1000 cells) were plated in 60 mm Petri dishes containing 2.7 ml of medium (modified McCoy's 5a medium containing 10% fetal bovine serum and 100 units/ml penicillin and 100 µg/ml streptomycin). The cells were incubated in a $CO_2$ incubator at 37° C. for 5 hours for attachment to the bottom of Petri dishes. Compounds were prepared fresh in medium at ten times the final concentration, and then 0.3 ml of this stock solution was added to the 2.7 ml of medium in the dish. The cells were then incubated with compounds for 72 hours at 37° C. At the end of incubation, the compound-containing media were decanted, the dishes were rinsed with 4 ml of Hank's Balance Salt Solution (HBSS), 5 ml of fresh medium was added, and the dishes were returned to the incubator for colony formation. The cell colonies were counted using a colony counter after incubation for 14 days for NCI/ADR-RES cells and 10 days for HCT116 cells and SF 295 cells. Cell survival was calculated and the $IC_{50}$ values (the drug concentration producing 50% inhibition of colony formation) were determined for each tested compound.

Results.

As revealed from the data presented in Table 18, D11B proved to be the most effective compound amongst the 12 compounds in killing human cancer cells.

TABLE 18

| Compound | $IC_{50}$ (nM) | | |
|---|---|---|---|
| | Glioblastoma | Colon Cancer | Breast Cancer |
| D11B | 176.9 | 166.7 | 1,312.5 |
| D15B | 228.9 | 258.3 | 1,375.0 |
| D16B | >5,000 | >5,000 | >5,000 |
| D17B | 750.0 | 826.9 | >5,000 |
| D18B | 1,833.3 | 2,000.0 | >5,000 |
| D19B | 3,500.0 | 3,461.5 | >5,000 |
| D20B | >5,000 | >5,000 | >5,000 |
| D21B | 2,166.7 | 3,615.4 | >5,000 |
| D23B | >5,000 | >5,000 | >5,000 |
| D24B | >5,000 | >5,000 | >5,000 |
| D25B | 204.6 | 158.3 | 1,458.3 |
| D35B | 280.8 | 360.4 | 1,708.3 |

HCT116 human colon cancer cells and SF 295 human glioblastoma cells were both more sensitive to D11B than the NCI/ADR-RES human breast cancer cells. Effective and significant killing of SF 295 human glioblastoma cells was of particular interest in that these cells are extremely resistant to many anticancer drugs and radiotherapy. These data indicate that while D11B and its derivatives are all bis-acridine intercalators, the unique chemical structure of D11B is responsible for its enhanced activity and specificity. Given the results observed for breast cancer cells compared to glioblastoma and colon cancer, it is expected that one or more of prostate, lung, or skin cancer cell lines will fail to respond to D11B, thereby further demonstrating selectivity for colon and glioblastoma cancer.

EXAMPLE 5

In Vivo Toxicity of D11B

The objective of this study was to determine the maximum tolerated doses of D11B as compared to selected D11B derivatives in normal C3H/HeN mice.

Methods.

The $MTD_{40}$ (maximum tolerated dose at day 40) values were determined on normal C3H/HeN mice using standard procedures. In consecutive type studies, two mice were dosed at low and moderate doses of 40 and 100 mg/kg. If no severe and irreversible toxicity (euthanasia was required) occurred at these doses, a new pair of animals was initiated at 180 mg/kg, which was 1.8 times higher than 100 mg/kg. Sequential dosages (i.e., two mice for each drug dose) were increased by a factor of 1.8 until severe and irreversible toxicity occurred, i.e., the animal became emaciated; the animal underwent rapid weight loss (cachexia, 20%) within several (2-4) days and euthanasia was required. If severe and irreversible toxicity occurred at these doses (i.e., euthanasia was required), a new pair of animals was initiated at 22.22 mg/kg, which was 1.8 times lower than 40 mg/kg. Sequential dosages (i.e., two mice for each drug dose) were reduced by a factor of 1.8 until no severe and irreversible toxicity occurred. The result of this exercise was two dosages, one apparently non-lethal and the other lethal, if severe and irreversible toxicity occurred and euthanasia was required. Six mice were dosed at each dosage. If no severe and irreversible toxicity occurred at the lower dosage and at least one with severe and irreversible toxicity at the higher dose, then the lower dose was considered to be the MTD.

Compounds were administered to C3H/HeN mice by intraperitoneal injection (5% alcohol, 5% CREMOPHOR® EL, and 90% saline, 0.5 ml/20 gram, single injection). Drug toxicity was evaluated on mice checked daily for 40 days. The toxicity parameters reported were the $MTD_{40}$. The MTD was defined as the highest dose causing no severe irreversible toxicity in one treatment group, but at least one animal exhibiting severe and irreversible toxicity and being euthanized at next higher dose. At the end of experiment, all mice were euthanized.

Results.

The results in Table 19 show that compounds D11B and D15B were significantly less toxic to mice than compounds D25B and D35B. Among the four compounds, D11B was the least toxic compound

TABLE 19

| Compound Names | MTD (mg/kg) |
|---|---|
| D11B | 450 |
| D15B | 250 |
| D35B | 12.5 |
| D25B | 6 |

These results indicate that D11B exhibits significantly lower toxicity to mice, compared with many conventional drugs used in the clinical setting. D11B's low toxicity dramatically enhances its therapeutic index thereby making it useful in the treatment of human cancer.

EXAMPLE 6

In Vivo Efficacy of D11B in Treating Colon Cancer

The objective of this study was to demonstrate the in vivo efficacy of D11B as compared to selected D11B derivatives on HCT116 human colon cancer xenografts.

Methods.

This in vivo anticancer efficacy study was performed on nude mice (nu/nu genotype) bearing HCT116 human colon cancer xenografts. These human tumors grew exponentially following implantation into the flanks of the mice and reached a diameter of 3 mm. Treatment was initiated at that time, with the first day of treatment designated as day 0 for all calculations and plots. The mice were injected i.p. with the different compound solutions (5% alcohol, 5% CREMOPHOR® EL, and 90% saline, 0.5 ml/20 g, single injection). Mice in the control group, bearing 3 mm diameter tumors, were treated with vehicle alone. After treatment, tumor sizes were measured by caliper every day. Daily measurement of the tumor diameters (d1, d2) in two orthogonal directions was used to calculate the tumor volume (tumor volume=$\pi/6\{(d1+d2)/2\}^3$) using the approximation that the tumors were spherical. The values of time (days) required to grow the tumor to the size of 1,000 cu. mm after various treatments and tumor growth delay percentage were calculated for evaluating the treatment effects. Survival times and tumor inhibitory effects on day 20 after treatment were also observed and recorded.

Figure 1:
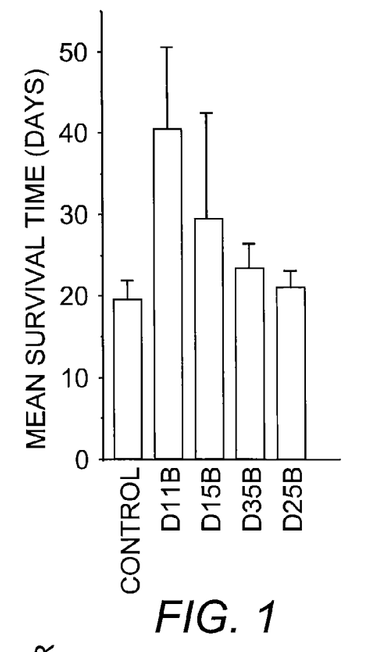
FIG. 1 shows the survival of nude mice bearing HCT116 human colon cancer xenografts after drug treatment.
Figure 2:
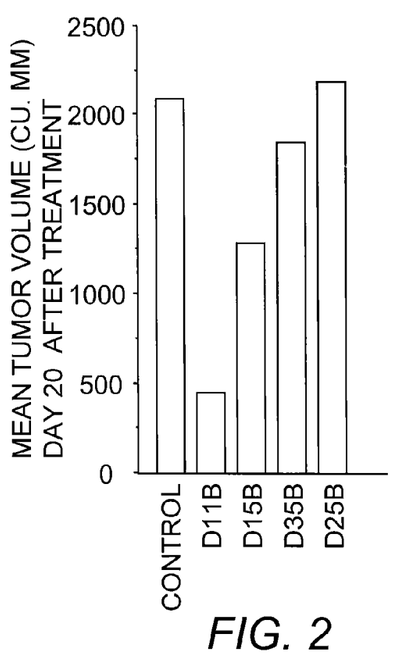
FIG. 2 shows the inhibitory effects of D11B and derivatives thereof on the growth of HCT116 human colon cancer xenografts 20 days after drug treatment.
Figure 3:
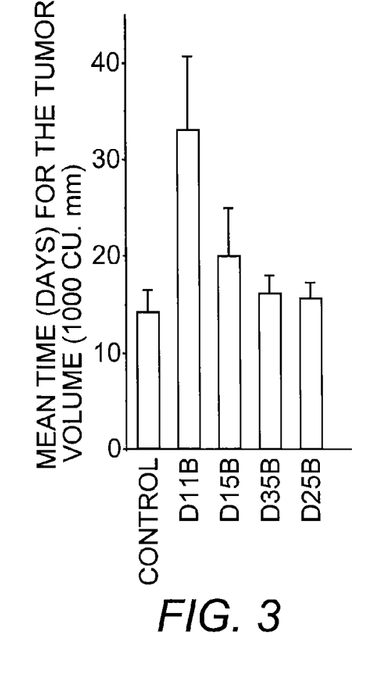
FIG. 3 shows the effects of D11B and derivatives thereof on the delay of the time for tumor volume of 1,000 cu. mm.

Results. As shown in FIGS. 1-3, D11B proved to be the most effective compound in inhibiting the growth of HCT116 human colon cancer xenografts among all compounds tested. The mice bearing HCT116 human colon cancer xenografts after treatment with D11B exhibited a mean survival time of 40.5 days, compared to 19.7 days in the control group (FIG. 1). The results in FIG. 2 show that treatment with D11B most effectively inhibited the growth of HCT116 human colon cancer xenografts on day 20 after drug administration. The inhibition ratios were 4.65 for D11B, 1.62 for D15B, 1.13 for D35B, and 0.96 for D25B. The FIG. 3 shows that D11B most significantly delayed the time for the growth of HCT116 human colon cancer xenografts up to the tumor volume of 1,000 cu. mm. The tumor growth delay percentages were 131% for D11B, 39.86% for D15B, 13.29% for D35B, and 9.79% for D25B. These results indicate that D11B exhibited the highest efficacy and lowest toxicity, exceeding D15B, and both D25B and D35B were ineffective in controlling the growth of HCT116 human colon cancer xenografts.

EXAMPLE 7

In Vivo Efficacy of D11B in Treating Glioblastoma

The objective of this study was to demonstrate the in vivo efficacy of D11B as compared to selected D11B derivatives on SF 295 human glioblastoma xenografts.

Methods.

In vivo anticancer efficacy studies were performed on nude mice (nu/nu genotype) bearing SF 295 human glioblastoma xenografts. These human tumors grew exponentially following implantation into the flanks of the mice and reached a diameter of 3 mm. Treatment was initiated at that time, with the first day of treatment designated as day 0 for all calculations and plots. The mice were injected i.p. with D11B and D11B derivative solutions (5% alcohol, 5% CREMOPHOR® EL, and 90% saline, 0.5 ml/20 g, single injection). Compound doses were 382 mg/kg for D11B, 212 mg/kg for D15B, 5 mg/kg for D25B, and 10.6 mg/kg for D35B. Mice in the control group bearing 3 mm diameter tumors was treated with vehicle alone. After treatment, tumor sizes were measured by caliper every day. Daily measurements of the tumor diameters (d1, d2) in two orthogonal directions was used to calculate the tumor volume (tumor volume=$\pi/6\{(d1+d2)/2\}^3$) using the approximation that the tumors were spherical. The values of time (days) required to grow the tumor to twice their initial size after various treatments was calculated as tumor doubling time (TDT) for evaluating the treatment effects. Survival times and curative effects after treatment were also observed and recorded.

Results.

Figure 4:
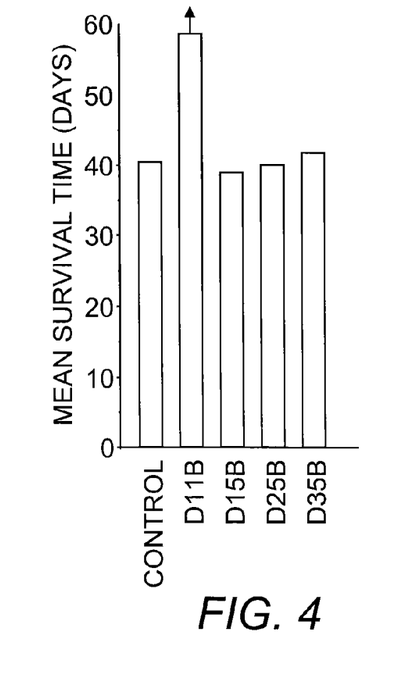
FIG. 4 shows the survival of nude mice bearing SF 295 human glioblastoma xenografts after drug treatment.
Figure 5:
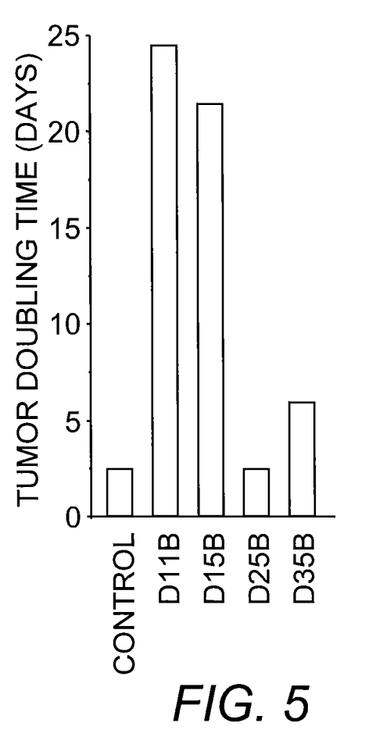
FIG. 5 shows the chemotherapeutic effects of D11B compared to D11B derivatives on SF 295 human glioblastoma xenografts after drug treatment.
Figure 6:
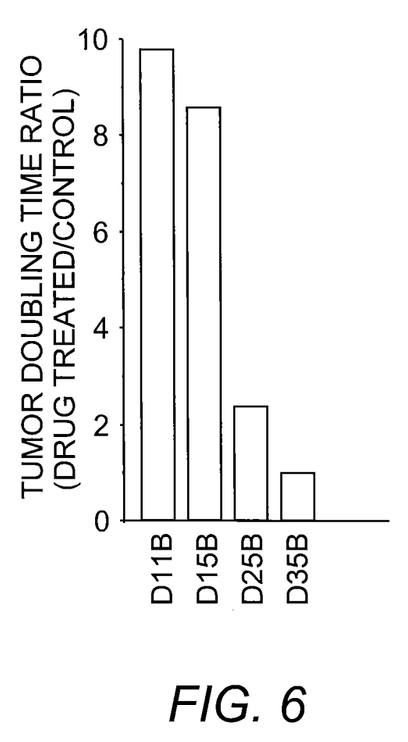
FIG. 6 shows the ratio of tumor doubling time of D11B compared to D11B derivatives in the treatment of SF 295 human glioblastoma xenografts.

As shown in the FIGS. 4-9, D11B proved to be the most effective compound in inhibiting the growth of SF 295 human glioblastoma xenografts amongst all compounds tested. Indeed, one mouse was even cured with D11B. The mice bearing SF 295 human glioblastoma xenografts after treatment with D11B exhibited a mean survival time for 58.67 days or longer, compared to 40.5 days in the control group (FIG. 4). Moreover, the results in FIGS. 5 and 6 indicated that treatment with D11B most effectively inhibited the growth of SF 295 human glioblastoma xenografts. The TDT (tumor doubling time) of the D11B-treated group was 24.5 days. The TDT of the control group was 2.5 days. The ratio of TDTs (D11B treated over control) was 9.8. These results demonstrate that D11B proved to be the least toxic to normal mice and extremely effective in controlling the growth of SF 295 human glioblastoma xenografts. The data further suggested that D11B exhibits selectivity in killing SF 295 human glioblastoma cells.

While D15B appeared to exhibit efficacy in controlling the growth of SF 295 human glioblastoma xenografts, it was observed that D15B caused lethal gastrointestinal toxicity in mice at late stage. Mice treated with D15B were severely ill because of its inhibition of gastrointestinal movement. Two mice died, one at day 36 and one at day 38. The results further showed that both D25B and D35B were ineffective in controlling of the growth of SF 295 human glioblastoma xenografts. The results were consistent with those obtained with HCT116 human colon cancer xenografts treated with both D25B and D35B.

EXAMPLE 8

Preparation of Bis-(Azoheterocyclic)-Intercalators Having Bis(4-Aminophenyl)Ether as a Tether Synthesis of bis-(azoheterocyclic)-intercalators (Scheme 4).

A mixture of bis(4-aminophenyl)ether (10 mmol, 1 equiv.) and aryl chloride (22 mmol, 2.2 equiv.) in 50-100 ml of iso-propanol was stirred and refluxed for 12 hours. The resulting suspension was cooled to room temperature, filtered, and washed with iso-propanol (3×20 ml). Drying at room temperature afforded the corresponding dihydrochloride. In some cases, TLC of the product showed two spots; the lower one was a di-substituted product and the higher one was a mono-substitute product. Pure di-substituted dihydrochlorides were obtained according to the following procedure. The dihydrochloride was suspended in a small amount of ethanol and refluxed for several minutes and hot solution was filtered. The solid component was enriched by the di-substituted product and the mother solution was enriched by the mono-substituted product. The procedure was repeated several times (TLC control $CHCl_3/MeOH/NH_4OH$, 100/10/1). The dihydrochloride was suspended in 50 ml of methanol and a solution of $Na_2CO_3$ 40 mmol (4 equiv) in 50 ml of water was added. The mixture was refluxed for 30 minutes, and methanol was evaporated. The resulting solid was filtered and washed with water (3×50 ml). Drying at room temperature afforded the desired product.

SCHEME 4

TABLE 20

| Cmpd | Structure | m.p. (° C.) | Yield |
|---|---|---|---|
| D244B | mw(C$_{22}$H$_{18}$N$_4$O) = 354.41 | 263-264 | 74% light-yellow powder |
| D245B | mw(C$_{30}$H$_{22}$N$_4$O) = 454.54 | 129-130 | 71.6% yellow powder |
| D254B | mw(C$_{36}$H$_{24}$N$_6$O) = 556.63 | 338-340 | 72.3% orange powder |

TABLE 20-continued

| Cmpd | Structure | m.p. (° C.) | Yield |
|---|---|---|---|
| D275 | mw(C₄₄H₃₀N₄O) = 630.76 | 114-115 | 61% light-green solid |
| D276 | mw(C₂₂H₁₆N₁₀O) = 436.44 | 372 | 86% off-white powder |
| D278 | mw(C₃₀H₂₂N₄O) = 454.54 | 110-112 | 50% off-white solid |
| D281 | mw(C₂₈H₂₀N₆O) = 456.51 | 124-125 | 98% off-white solid |
| D284 | mw(C₂₈H₂₀N₆O) = 456.51 | 362 | 93.6% beige powder |
| D288 | mw(C₃₂H₂₆N₄O) = 482.59 | 123-124 | 93.5% off-white powder |

EXAMPLE 9

In Vitro Anti-Colon Cancer Activity of Bis-(Azoheterocyclic)-Intercalators

The objective of this study was to determine anticancer activity on HCT116 human colon cancer cells of bis-(azoheterocyclic)-intercalators having the same bis(4-aminophenyl) ether tether as D11B.

Methods.

Four hundred HCT116 cells were plated in 60 mm Petri dishes containing 2.7 ml of medium (modified McCoy's 5a medium containing 10% fetal bovine serum and 100 units/ml penicillin and 100 µg/ml streptomycin). The cells were incubated in a $CO_2$ incubator at 37° C. for 5 hours for attachment to the bottom of Petri dishes. Compounds were prepared fresh in medium at ten times the final concentration, and then 0.3 ml of this stock solution was added to the 2.7 ml of medium in the dish. The cells were then incubated with drugs for 72 hours at 37° C. At the end of incubation the compound-containing media were decanted, the dishes were rinsed with 4 ml of Hank's Balance Salt Solution (HBSS), 5 ml of fresh medium was added, and the dishes were returned to the incubator for colony formation. HCT116 cell colonies were counted using a colony counter after 24 days of incubation. Cell survival was calculated and $IC_{50}$ values were determined for each compound tested.

Results.

As shown in Table 21, all compounds tested were effective in killing human colon cancer cells. Compounds D244, D245, and D254 were salt forms. Among the three salt forms, D245 was most effective in killing HCT116 cells. Compounds 244B, 245B and 254B were base forms. Among the three base forms, 245B was again the most effective compound in killing HCT116 cells.

TABLE 21

| Compound | $IC_{50}$ (nM) |
|---|---|
| D244 | 4,217 |
| D245 | 122 |
| D254 | 1,460 |
| 244B | 3,339 |
| 245B | 79 |
| 254B | 722 |

In general, the three base compounds were more active than their corresponding salt forms against HCT116 human colon cancer cells. These results indicate that, similar to D11B, compound 245 will be useful in the treatment of human colon cancer. In this respect, it is expected that D245B will exhibit in vivo activity in a colon cancer mouse xenograft model system.

EXAMPLE 10

In Vitro Anti-Colon Cancer Activity of Bis-(Azoheterocyclic)-Intercalators

The objective of this study was to determine the anticancer activity on SF 295 human glioblastoma cells of bis-(azoheterocyclic)-intercalators having the same bis(4-aminophenyl) ether tether as D11B.

Methods.

One thousand SF 295 cells were plated in 60 mm Petri dishes containing 2.7 ml of medium (modified McCoy's 5a medium containing 10% fetal bovine serum and 100 units/ml penicillin and 100 µg/ml streptomycin). The cells were incubated in a $CO_2$ incubator at 37° C. for 5 hours for attachment to the bottom of Petri dishes. Compounds were prepared fresh in medium at ten times the final concentration, and then 0.3 ml of this stock solution was added to the 2.7 ml of medium in the dish. The cells were then incubated with the compounds for 72 hours at 37° C. At the end of incubation, the compound-containing media were decanted, the dishes were rinsed with 4 ml of Hank's Balance Salt Solution (HBSS), 5 ml of fresh medium was added, and the dishes were returned to the incubator for colony formation. After incubation for 10 days, the cell colonies were counted using a colony counter. Cell survival was calculated and the values of $IC_{50}$ were determined for each compound tested.

Results.

As shown in Table 22, compounds D245B, D275, and D288 were effective in killing SF 295 human glioblastoma cells. The other four compounds were ineffective in the inhibition of the growth of SF 295 human glioblastoma cells.

TABLE 22

| Compound | $IC_{50}$ (nM) |
|---|---|
| D245B | 132.7 |
| D275 | 1,416.7 |
| D276 | >5,000 |
| D278 | >5,000 |
| D281 | >5,000 |
| D284 | >5,000 |
| D288 | 85 |

Among the three effective compounds, D288 was the most effective against SF 295 cells, indicating that D288 would exhibit efficacy and reduced toxicity in vivo. It is noted that cytotoxic effects of compounds D245B on SF 295 cells were similar to its effects on HCT116 human colon cancer cells ($IC_{50}$=122 nM). These results indicate that, similar to D11B, compounds D245 and D288 will be useful in the treatment of human glial cancers. In this respect, it is expected that D245 and D288 will exhibit in vivo activity in a glioblastoma mouse xenograft model system.

EXAMPLE 11

In Vivo Toxicity of D245 and D288

The objective of this study was to determine the acute toxicity of D245B and D288 compounds in normal mice.

Methods.

The $MTD_{40}$ values of D245B and D288 were determined on normal C3H/HeN mice using standard procedures. D245B and D288 were prepared in a suspension formulation (alcohol:CREMOPHOR EL:saline [5%:5%:90%]) and administered to C3H/HeN mice by single intraperitoneal injection. In the consecutive type studies, two mice were dosed at low and moderate doses of 40 and 100 mg/kg. Severe and irreversible toxicity (animal becomes emaciated; animal undergoes rapid weight loss (20%) within 2-4 days; euthanasia was required) occurred at these two doses, a new pair of animals was tested at a dose of 25 mg/kg, which was 1.6 times lower than 40 mg/kg. No severe and irreversible toxicity occurred at the dose of 25 mg/kg. The result of this exercise was two dosages, one apparently nonlethal and the other lethal (severe and irreversibly toxic). Six mice were dosed at each dosage. No severe and irreversible toxicity occurred at the dose of 25 mg/kg, but severe and irreversible toxicity occurred at the dose of 40 mg/kg. Therefore, the dose of 25 mg/kg was considered to be the MTD. Drug toxicity was evaluated on mice checked daily for 40 days. The toxicity parameters reported were the $MTD_{40}$. At the end of experiment, all mice will be euthanized.

Results.

As shown in the following Table 23, the values of $MTD_{40}$ of both D245B and D288 were 25 mg/kg in normal C3H/HeN mice. These values serve as important toxic parameters and can be employed in preclinical studies, including efficacy studies in nude mice and toxicity studies in normal animals.

TABLE 23

| Compound Name | Values of $MTD_{40}$ (mg/kg) |
| --- | --- |
| D245B | 25 |
| D288 | 25 |

What is claimed is:

1. A method for selectively decreasing colon or glial tumor cell proliferation comprising contacting a colon or glial tumor cell with an effective amount of a compound of Formula I:

wherein dashed lines represent bonds that are independently present or absent, thereby selectively decreasing the proliferation of the colon or glial tumor cell as compared to a control.

2. The method of claim 1, wherein the compound of Formula I is a diglycolate salt.

3. The method of claim 1, wherein the glial tumor cell is an astrocytoma tumor cell, ependymal tumor cell, glioblastoma multiforme tumor cell, or primitive neuroectodermal tumor cell.

4. A method for increasing survival time of a subject with cancer comprising administering to a subject with colon cancer or glioma an effective amount of a compound of Formula I:

wherein dashed lines represent bonds that are independently present or absent, thereby increasing the survival time of the subject as compared to a subject not receiving said treatment.

5. The method of claim 4, wherein the compound of Formula I is a diglycolate salt.

6. The method of claim 4, wherein the glioma is an astrocytoma, ependymal tumor, glioblastoma multiforme, or primitive neuroectodermal tumor.

7. The method of claim 5, wherein the glioblastoma multiforme is located in the brain of the subject.

8. The method of claim 5, wherein the glioblastoma multiforme is located in the spinal cord of the subject.

9. The method of claim 4, wherein the subject is a mammal.

10. The method of claim 9, wherein the mammal is a human subject.

11. The method of claim 4, wherein said administering is carried out orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes.

12. A method for treating colon cancer or glioma comprising administering to a subject in need thereof an effective amount of a compound of Formula I:

wherein dashed lines represent bonds that are independently present or absent, thereby treating the subject's colon cancer or glioma.

13. The method of claim 12, wherein the compound of Formula I is a diglycolate salt.

14. The method of claim 12, wherein the glioma is an astrocytoma, ependymal tumor, glioblastoma multiforme, or primitive neuroectodermal tumor.

15. The method of claim 14, wherein the glioblastoma multiforme is located in the brain of the subject.

16. The method of claim 14, wherein the glioblastoma multiforme is located in the spinal cord of the subject.

17. The method of claim 12, wherein the subject is a mammal.

18. The method of claim 17, wherein the mammal is a human subject.

19. The method of claim 12, wherein said administering is carried out orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes.

20. A composition comprising:

wherein dashed lines represent bonds that are independently present or absent.

21. The composition of claim 20, further comprising a pharmaceutically acceptable carrier.

22. The composition of claim 20, wherein said composition is formulated for administration orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes.

* * * * *